(12) United States Patent
Iwamoto et al.

(10) Patent No.: US 12,188,942 B2
(45) Date of Patent: Jan. 7, 2025

(54) METHOD FOR IMPROVING RESULT MONOCLONAL ANTIBODY DETECTION

(71) Applicant: SHIMADZU CORPORATION, Kyoto (JP)

(72) Inventors: Noriko Iwamoto, Kyoto (JP); Takashi Shimada, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 135 days.

(21) Appl. No.: 16/958,477

(22) PCT Filed: Dec. 28, 2017

(86) PCT No.: PCT/JP2017/047241
§ 371 (c)(1),
(2) Date: Jun. 26, 2020

(87) PCT Pub. No.: WO2019/130549
PCT Pub. Date: Jul. 4, 2019

(65) Prior Publication Data
US 2021/0003587 A1    Jan. 7, 2021

(51) Int. Cl.
*G01N 33/68* (2006.01)
*G01N 30/02* (2006.01)
*G01N 33/537* (2006.01)

(52) U.S. Cl.
CPC ......... *G01N 33/6848* (2013.01); *G01N 30/02* (2013.01); *G01N 33/5375* (2013.01); *G01N 33/6857* (2013.01); *G01N 2030/027* (2013.01)

(58) Field of Classification Search
None
See application file for complete search history.

(56) References Cited

U.S. PATENT DOCUMENTS

| 2016/0252522 A1 | 9/2016 | Shimada et al. |
| 2018/0051053 A1 | 2/2018 | Shimada et al. |

(Continued)

FOREIGN PATENT DOCUMENTS

| EP | 3 495 480 | 6/2019 | |
| FR | 3165922 | * 5/2017 | ............. G01N 33/50 |

(Continued)

OTHER PUBLICATIONS

International Search Report issued Mar. 27, 2018 in International (PCT) Application No. PCT/JP2017/047241.

(Continued)

*Primary Examiner* — Xiaoyun R Xu
(74) *Attorney, Agent, or Firm* — Wenderoth, Lind & Ponack, L.L.P.

(57) ABSTRACT

The present invention provides a detection method for a monoclonal antibody in a sample, comprising: (a) a step of capturing the monoclonal antibody in the sample and immobilizing the monoclonal antibody in pores of a porous body; (b) a step of bringing the porous body in which the monoclonal antibody is immobilized with nanoparticles on which protease is immobilized to conduct selective protease digestion of the monoclonal antibody; (c) a step of detecting, by a liquid chromatography mass spectrometry (LC-MS), peptide fragments obtained by the selective protease digestion; and (a') a step of conducting a reduction reaction under an acidic condition after the step (a). By the present invention, further applicability of the detection method for the monoclonal antibodies using mass spectrometry is expected.

4 Claims, 5 Drawing Sheets

Specification includes a Sequence Listing.

(56) References Cited

U.S. PATENT DOCUMENTS

| | | | |
|---|---|---|---|
| 2018/0051272 A1 | 2/2018 | Shimada et al. | |
| 2018/0052172 A1 | 2/2018 | Shimada et al. | |
| 2018/0059074 A1 | 3/2018 | Shimada et al. | |
| 2018/0148763 A1 | 5/2018 | Shimada et al. | |

FOREIGN PATENT DOCUMENTS

| | | |
|---|---|---|
| WO | 2015/033479 | 3/2015 |
| WO | 2016/143223 | 9/2016 |
| WO | 2016/143224 | 9/2016 |
| WO | 2016/143226 | 9/2016 |
| WO | 2016/143227 | 9/2016 |
| WO | 2016/194114 | 12/2016 |
| WO | 2018/025346 | 2/2018 |

OTHER PUBLICATIONS

Written Opinion of the International Searching Authority issued Mar. 27, 2018 with machine translation.

Noriko Iwamoto et al., "Selective detection of complementarity determining regions of monoclonal antibody by limiting protease access to the substrate: nano-surface and molecular-orientation limited proteolysis", Anaylst, Feb. 7, 2014, pp. 576-580.

Noriko Iwamoto et al., "The development of the validated LCMS bioanalysis of trastuzumab in human plasma using a selective detection method for complementarity-determining regions of monoclonal antibodies: nano-surface and molecular-orientation limited (nSMOL) proteolysis", Analytic Methods, 2015, pp. 9177-9183.

Noriko Iwamoto et al., "Fully validated LCMS bioanalysis of Bevacizumab in human plasma using nano-surface and molecular-orientation limited (nSMOL) proteolysis", Drug Metabolism and Pharmacokinetics, 2016, pp. 46-50.

Noriko Iwamoto et al., "Application of nano-surface and molecular-orientation limited proteolysis to LC-MS bioanalysis of cetuximab", Bioanalysis, 2016, pp. 1009-1020.

Noriko Iwamoto et al., "Validated LC/MS Bioanalysis of Rituximab CDR Peptides Using Nano-surface and Molecular-Orientation Limited (nSMOL) Proteolysis", Biol. Pharm. Bull., 2016, vol. 39, No. 7, pp. 1187-1194.

Noriko Iwamoto et al., "Validated LC-MS/MS analysis of immune checkpoint inhibitor Nivolumab in human plasma using a Fab peptide-selective quantitation method: nano-surface and molecular-orientation limited (nSMOL) proteolysis", Journal of Chromatography B, 2016, pp. 1023-1024.

Noriko Iwamoto et al., "Multiplex LCMS Bioanalysis of Brentuximab Vedotin, Rituximab and Cetuximab towards Therapeutic Drug Monitoring Application by Combined Calibration Curve Using Fab-Selective Limited Proteolysis nSMOL", Clinical Pharmacology & Biopharmaceutics, 2016, vol. 5, Issue 4.

Noriko Iwamoto et al., "LC-MS bioanalysis of Trastuzumab and released emtansine using nano-surface and molecular-orientation limited (nSMOL) proteolysis and liquid-liquid partition in plasma of Trastuzumab emtansine-treated breast cancer patients", Journal of Pharmaceutical and Biomedical Analysis, 2017, pp. 33-39.

Office Action issued May 9, 2022 in corresponding Chinese Patent Application No. 201780097953.6, with machine English translation.

Zhao, J. et al., "Characterization of the size variants of a recombinant humanized monoclonal antibody (rhumAb1)", Acta Pharmaceutica Sinica, 2016, vol. 51, No. 12, pp. 1897-1905, with machine English translation.

Pang, Y. et al., "Pepsin-Containing Membranes for Controlled Monoclonal Antibody Digestion Prior to Mass Spectrometry Analysis", Anal Chem., 2015, vol. 87, Issue. 21, pp. 10942-10949.

Iwamoto, N. et al., "Validated LC-MS/MS analysis of immune checkpoint inhibitor Nivolumab in human plasma using a Fab peptide-selective quantitation method: nano-surface and molecular-orientation limited (nSMOL) proteolysis", Journal of Chromatography B, 2016, vols. 1023-1024, pp. 9-16.

Office Action issued Jan. 5, 2023 in corresponding Chinese Patent Application No. 201780097953.6, with machine translation, 16 pages.

* cited by examiner

METHOD FOR IMPROVING RESULT MONOCLONAL ANTIBODY DETECTION

TECHNICAL FIELD

The present invention relates to a method for improving detection results in quantification of monoclonal antibody using mass spectrometry. Still more specifically, the present invention relates to improvement of a protocol that has been established for quantification of a monoclonal antibody.

BACKGROUND ART

Recently, intensive efforts have been made to develop bio-analysis of antibody medicines by using LC-MS/MS technique as a quantification method in replacement of ELISA technique.

The group of the present inventors have found that protease digestion of a monoclonal antibody by a site-selective solid phase-solid phase reaction is possible by immobilizing both of the monoclonal antibody to be measured and a protease capable of digesting the monoclonal antibody as a substrate onto a solid phase, thereby successfully obtaining peptides specific to individual monoclonal antibodies (see Patent Literatures 1 to 6, and Non-Patent Literatures 1 to 8). This method is a pretreatment method for mass spectrometry in which selective protease digestion of a monoclonal antibody is carried out in such a manner that a porous body having the monoclonal antibody immobilized in pores thereof is brought into contact with nanoparticles having a protease immobilized thereon in a liquid, and is a groundbreaking technology that allows effective detection and quantification of obtained peptide fragments by liquid chromatography mass spectrometry (LC-MS). The present inventors named this method as "nano-surface and molecular-orientation limited proteolysis method (nSMOL method) ."

Quantification of a blood level of an antibody medicine by the nSMOL method is a method that carries out trypsin digestion selectively digesting only the Fab region having a sequence specific to the antibody medicine and that inhibits the ion suppression effect most problematic in the LC-MS/MS analysis, thereby making it possible to provide more stable and highly reliable quantification values. The present inventors have already confirmed that a method for detecting a monoclonal antibody using a combination of the nSMOL method and the LC-MS/MS method meets the standards of the guidelines for validation of biological analysis methods in Japan, the United States, and Europe, in terms of measuring blood levels of 15 or more kinds of antibody medicines.

On the other hand, it is known that proteins, which are biopolymers, include some proteins having a very characteristically rigid structure. For example, it is known that the action of Amyloid beta, transferrin, and multiple transmembrane proteins (such as Rhodopsin and transporters) are controlled by having a rigid structure, even though the mechanisms of the controls are different.

One of such a structure to keep the rigidity of the protein structure is a cystine knot structure in which a knot-like structure is formed by SS bond. Examples of molecules having the cystine knot structure and contributing to specific signal transmission include cytokines such as vascular endothelial growth factor (VEGF) and interleukins.

Antibody molecules are high-molecular weight tetramer proteins consisting of two heavy chains and two light chains, each of which has an antibody-specific amino acid sequence with variable regions defining the diversity and function of the antibody and constant regions having the same molecular structure. Among the variable regions, complementarity determining regions (CDR) are regions in which mutation frequency is especially high, thereby determining the binding property with antigens. Between the CH1 domain and the CH2 domain in the heavy chain constant region, a structure called a hinge exists, which has a highly flexible structure.

The presence of the hinge in the antibody molecule secures 3-dimensional fluctuation of the fragment antigen binding (Fab) region. Molecular dynamics analysis such as nuclear magnetic resonance (NMR) analysis has shown that the Fc region is almost constant 3-dimensionally but Fab region is so largely fluctuated that Fab cannot be 3-dimensionally assigned. Once an antigen binds to Fab, the fluctuation decreases, thereby forming a rigid structure.

Antibody molecules have a lot of in-molecular and inter-molecular SS bonds, which play a role in physically supporting each region. It is deduced that oxidation-reduction potentials of sulfur atoms participating to the SS bond are different depending on the antibody molecules themselves or surrounding fine structure environments, so that each SS bond may have a different SS bond intensity.

CITATION LIST

Patent Literatures

Patent Literature 1: International Publication No. 2015/033479
Patent Literature 2: International Publication No. 2016/194114
Patent Literature 3: International Publication No. 2016/143224
Patent Literature 4: International Publication No. 2016/143223
Patent Literature 5: International Publication No. 2016/143226
Patent Literature 6: International Publication No. 2016/143227

Non Patent Literature

Non Patent Literature 1: Analyst. 2014 Feb. 7; 139(3):576-80. doi:10.1039/c3an02104a
Non Patent Literature 2: Anal. Methods, 2015; 21:9177-9183. doi:10.1039/c5ay01588j
Non Patent Literature 3: Drug Metabolism and Pharmacokinetics, 2016; 31:46-50. doi:10.1016/idmpk.2015.11.004
Non Patent Literature 4: Bioanalysis. 2016; 8(10):1009-20. doi:10.4155. bio-2016-0018
Non Patent Literature 5: Biol Pharm Bull, 2016; 39(7):1187-94. doi:10.1248/bpb.b16-00230
Non Patent Literature 6: Chromatogr B Analyt Technol Biomed Life Sci; 2016; 1023-1024:9-16. doi:10.1016/j.jchromb.2016.04.038
Non Patent Literature 7: Clin Pharmacol Biopharm 2016; 5:164. doi:10.4172/2167-065X.1000164
Non Patent Literature 8: J. Pharm Biomed Anal; 2017; 145:33-39. doi:10.1016/j.jpba.2017.06.032

SUMMARY OF INVENTION

Technical Problem

The nSMOL method is based on a reaction mechanism in which a protease immobilized on the surface of the nanoparticles of about 200 nm in diameter is brought into contact with immunoglobulin molecules immobilized on a porous body with pore diameter of about 100 nm, so that Fab of the immunoglobulin molecules are selectively cleaved in restricted reaction field. The nSMOL method is excellent in accuracy, sensitivity, and reproducibility. For performing the nSMOL method, the "nSMOL Antibody BA kit" (Shimadzu Corporation), which is a pretreatment kit for LC/MS/MS, has been commercially available with a protocol, for which the present inventors have diligently studied for improvement or the like of the protocol in order to further expand the versatility of the nSMOL method.

Under such circumstances, the present inventors confirmed that some monoclonal antibodies used as antibody medicines provide extremely lower detection results than other monoclonal antibodies. In consideration of high accuracy and sensitivity of the nSMOL method, it is believed that the low detection results would not be so problematic in clinical applications in many cases, but it is considered that there is a possibility that the process can be further improved to detect a very low antibody concentration with a higher reliability.

Solution to Problem

While not wishing to be bound by any theory, the present inventors predicted a possibility that the low detection result may be caused by the protease tolerance due to the rigidity of the antibody molecule to be analyzed. That is, the present inventors deduced a possibility that there is a highly rigid region in such an antibody molecule due to some mechanism, such as an existence of the cysteine knot structure by SS bond, for example, thereby giving the antibody molecule tolerance against protease, as a result of which the protease digestion expected in the nSMOL method does not proceed.

The nSMOL method is, by theory, configured to perform 3-dimensional control of the contact site of a substrate with the protease, and the protease reaction is expected to selectively proceed for Fab regions of any antibody. It has been already proved that the reaction surely proceeds regardless of the diversity of antibodies. However, in the case where the antibody molecule per se is highly rigid, there is a possibility that hydrolysis by protease allowing antibody quantification does not proceed, even if protease is brought into contact with the substrate.

In order to apply the nSMOL method to any monoclonal antibody medicine, various analysis conditions for such rigid monoclonal antibodies have been diligently studied. As a result, the present inventors found that, after fractionating the antibody molecules from a sample, 3-dimensional fluctuation can be attained in the molecules by quickly dissociating SS bonds by oxidation-reduction condition, thereby significantly improving the detection results by the nSMOL method. Since the oxidation-reduction condition does not dissociate the binding of protein A and Fc, the cysteine knot structure can be loosen while maintaining the antibody molecule on the porous body.

That is, the present invention provides the followings.
1. A detection method for a monoclonal antibody in a sample, comprising:
   (a) capturing monoclonal antibodies in a sample to immobilize the monoclonal antibodies in pores of a porous body;
   (b) bringing the porous body in which the monoclonal antibodies are immobilized with nanoparticles on which protease is immobilized to conduct selective protease digestion of the monoclonal antibodies;
   (c) detecting, by a liquid chromatography mass spectrometry (LC-MS), peptide fragments obtained by the selective protease digestion; and (a') after the step (a), conducting a reduction reaction under an acidic condition.
2. The method according to 1 above, wherein the step (a') is conducted by incubation in the presence of an organophosphorus-based reducing agent.
3. The method according to 2 above, wherein the organophosphorus-based reducing agent is Tris(2-carboxyethyl)phosphine (TCEP) or a hydrochloride salt thereof.
4. The method according to 3 above, wherein a concentration of the TCEP is in a range of 100 to 500 mM.
5. The method according to any one of 1 to 4 above, wherein the step (a') is conducted under a strong acidic condition of pH 2.5 or less.
6. The method according to any one of 1 to 5 above, wherein a time length of the reduction reaction of the step (a') is in a range of 10 to 60 min.
7. The method according to any one of 1 to 6 above, wherein the peptide fragments to be detected by the LC-MS are derived from a heavy chain.

Advantageous Effects of Invention

The present invention establishes a quantification method that allows analysis validation for monoclonal antibodies expected to have a chemically rigid structure, such as Tocilizumab and Mogamulizumab, thereby making the nSMOL method applicable for a wider range of antibodies than the conventional nSMOL method.

DESCRIPTION OF EMBODIMENTS

The present invention provides a detection method for a monoclonal antibody in a sample, comprising:
  (a) a step of capturing the monoclonal antibody in the sample and immobilizing the monoclonal antibody in pores of a porous body;
  (b) a step of bringing the porous body in which the monoclonal antibody is immobilized with nanoparticles on which protease is immobilized to conduct selective protease digestion of the monoclonal antibody;
  (c) a step of detecting, by a liquid chromatography mass spectrometry (LC-MS), peptide fragments obtained by the selective protease digestion; and
  (a') a step of conducting a reduction reaction under an acidic condition after the step (a).

<Step (a)>

Step (a) of the method according to the present invention is a step of capturing and immobilizing, in pores of a porous body, the monoclonal antibody in the sample.

In this Description, a "sample" means a liquid sample in which the presence of a monoclonal antibody is to be detected, and is not particularly limited. In general, the sample is a biological sample derived from a mammal such as a mouse, a rat, a rabbit, a goat, a bovine, a human being, or the like, especially a human subject, or mainly a human patient, or preferably plasma, serum, or a tissue homogenate extract. Alternatively, the sample may be a liquid sample containing a monoclonal antibody and serum artificially added, to prove the effect of the present invention. For detecting a monoclonal antibody in a method according to the present invention, a concentration of the monoclonal antibody in the sample should be in the range of 0.05 to 300 µg/ml.

Examples of the monoclonal antibody that can be a measurement target include, but not limited to, human antibodies such as panitumumab, ofatumumab, golimumab, ipilimumab, nivolumab, Ramucirumab, adalimumab, and the like; humanized antibodies such as Tocilizumab, trastuzumab, trastuzumab-DM1, bevacizumab, omalizumab, Mepolizumab, gemtuzumab, palivizumab, Ranibizumab, certolizumab, ocrelizumab, Mogamulizumab, Eculizumab, tocilizumab, mepolizumab, and the like; chimeric antibodies such as rituximab, cetuximab, infliximab, Basiliximab, and the like.

Furthermore, a conjugate having an additional function added while maintaining the specificity of a monoclonal antibody, for example, Fc-fused proteins (such as etanercept, abatacept, and the like) and antibody-drug conjugates (such as brentuximab vedotin, Gemtuzumab ozogamicin, Trastuzumab emtansine, and the like) may also be a monoclonal antibody as a measurement target. The conjugate may be pretreated to dissociate its bonding prior to the measurement, so that only its antibody portion can be provided to the analysis. As an alternative, the conjugate as such may be provided to the analysis.

Information on amino acid sequences of monoclonal antibodies, and the like can be obtained from, for example, Kyoto Encyclopedia of Genes and Genomes, KEGG.

The porous body for use in the method according to the present invention may be a material having a large number of pores and being capable of binding with an antibody site-specifically. An average pore diameter of the porous body is approximately in range of 10 nm to 200 nm, and set as appropriate to be smaller than the average particle diameter of the nanoparticles.

In step (a) in the present invention, a monoclonal antibody as a measurement target is immobilized in pores of a porous body. For this purpose, a porous body, in pores of which linker molecules interactive with the antibody site-specifically are immobilized may be preferably used.

The linker molecules may be preferably Protein A, Protein G, or the like, capable of site-specifically binding with the Fc domain of the antibody. The use of a porous body with such linker molecules immobilized in the pores thereof allows the Fc domain of the antibody to be anchored in the pores in such a way that the Fab domain is located near the surface layer in the pores, thereby allowing site-selective digestion of the Fab domain by the protease.

A porous body that can be suitably used in the present invention is not particularly limited. For example, Protein G Ultralink resin (manufactured by Pierce Corporation), Toyopearl TSKgel (manufactured by TOSOH Corporation), Toyopearl AF-rProtein A HC-650F resin (manufactured by TOSOH Corporation), Protein A Sepharose (GE Healthcare), KanCapA (KANEKA), and the like can be used.

A method for immobilizing an antibody in pores of a porous body is not particularly limited. For example, when an antibody is immobilized in a porous body in which Protein A or Protein G is immobilized in pores in advance, the antibody can be easily immobilized in pores by mixing a suspension of the porous body with a solution containing the antibody. A quantitative ratio of the porous body to the antibody can be appropriately set according to a purpose.

<Step (a')>

The method according to the present invention comprises, after the step (a), a step (a') of conducting a reduction reaction under an acidic condition.

The reduction reaction under an acidic condition may be conducted by incubation in the presence of an organophosphorus-based reducing agent, for example. Examples of the organophosphorus-based reducing agent include Tris(2-carboxyethyl)phosphine (TCEP) or a hydrochloride salt thereof, tributyl phosphine, and the like. These reducing agents are available from Sigma-Aldrich Co. LLC, NACALAI TESQUE, INC., Funakoshi Co., Ltd., and other suppliers. The suitable concentration of TCEP is preferably in the range of 100 to 500 mM in a reaction solution.

The reduction reaction of step (a') is preferably conducted under such a strong acidic condition of pH 2.5 or lower, such as pH 1.5, pH 2.0, and pH 2.5. The time length of the reduction reaction may be, but not limited to, in the range of 10 to 60 min, such as 20 min, 30 min, 40 min, 45 min, and 50 min. It is possible to conduct the reduction reaction for a time length longer than 60 min, but such a long time length is not so practical because the operation time for measurement becomes too long. The reaction temperature may be, but not limited to, from 15 to 30° C., and the reaction may be conducted at room temperature. Preferably, the reaction temperature may be about 25° C.

It should be noted that, this Description reads that the step (a') is conducted after the step (a), for the sake of better understanding of the method according to the present invention, but, as a person skilled in the art would readily understand, these steps may include various operations in general such as addition and removal of reagents and washing, and therefore the reduction reaction under the acidic condition described as the step (a') would be possibly conducted before an operation explained as part of the step (a) in some cases. However, it would be understood that the "step of conducting a reduction reaction under an acidic condition" described as the step (a') is conducted after the "step of capturing the monoclonal antibody in the sample and immobilizing the monoclonal antibody in pores of a porous body" described above as the step (a) and before the "step of bringing the porous body in which the monoclonal antibody is immobilized with nanoparticles on which protease is immobilized to conduct selective protease digestion of the monoclonal antibody" described below as the step (b).

<Step (h)>

Step (b) of the method according to the present invention is a step of carrying out selective protease digestion of the monoclonal antibody by contacting the porous body with nanoparticles, the porous body being obtained in step (a) to have the monoclonal antibody immobilized thereon, and the nanoparticles having a protease immobilized thereon.

The protease to be immobilized on nanoparticles may be appropriately selected depending on the types of the monoclonal antibody to be quantified or identified by mass spectrometry, and is not limited. Examples of the protease include trypsin, chymotrypsin, lysyl endopeptidase, V8 protease, Asp N protease (Asp-N), Arg C protease (Arg-C), papain, pepsin, dipeptidyl peptidase used alone or in combination. As the proteases, trypsin is particularly preferably used. Examples of the protease that can be suitably used in the method of the present invention include Trypsin Gold (manufactured by Promega Corporation), Trypsin TPCK-Treated (manufactured by Sigma Corporation), and the like.

The nanoparticles have a larger average particle size than the average pore diameter of the porous body. The shape of the nanoparticles are not particularly limited. However, from a point of view of homogenization of access of the protease to the pores of the porous body, spherical nanoparticles are preferred. Further, it is preferable that the nanoparticles have high dispersibility and a uniform particle size.

As a type of the nanoparticles, magnetic nanoparticles that can be dispersed or suspended in an aqueous medium and can be easily recovered from the dispersion or suspension by magnetic separation or magnetic precipitation separation are preferable. Further, from a point of view that aggregation is less likely to occur, magnetic nanoparticles coated with an organic polymer are more preferable. Specific examples of magnetic nanobeads coated with an organic polymer include FG beads, SG beads, Adembeads, nanomag, and the like. As a commercially available product, for example, FG beads (polymer magnetic nanoparticles having a particle size of about 200 nm obtained by coating ferrite particles with polyglycidyl methacrylate (poly GMA)) manufactured by Tamagawa Seiki Co., Ltd. is suitably used.

In order to suppress nonspecific protein adsorption and to selectively immobilize the protease, the nanoparticles are preferably modified with spacer molecules capable of binding to the protease. By immobilizing a protease via a spacer molecule, desorption of the protease from surfaces of the nanoparticles is suppressed, and site-selectivity of protease digestion can be improved. Further, by adjusting a molecular size of a spacer, a protease can be selectively access a desired position of an antibody, and thus site-selectivity can be improved.

Nanoparticles surface-modified with such spacer molecules are also commercially available, for example, nanoparticles modified with a spacer molecule having an ester group activated with N-hydroxysuccinimide (active ester group) are commercially available under a trade name of "FG beads NHS" (Tamagawa Seiki Co., Ltd.).

A method for immobilizing a protease on surfaces of nanoparticles is not particularly limited. An appropriate method can be adopted according to characteristics of the protease and the nanoparticles (or spacer molecules modifying the surfaces of the nanoparticles). The aforementioned pretreatment kit for LC/MS/MS "nSMOL Antibody BA Kit" (Shimadzu Corporation) includes "FG beads Trypsin DART®", which are nanoparticles on which trypsin is immobilized as a protease, which can suitably be used for the method of the present invention.

By contacting the porous body having the monoclonal antibody immobilized thereon with the nanoparticles having the protease immobilized thereon, the selective protease digestion of the monoclonal antibody is carried out, thereby producing peptide fragments.

For example, the protease digestion may be carried out in a buffer solution adjusted to be near optimum pH for the protease. The reaction temperature for the protease digestion may be at about 37° C., but it is preferable to carry out the protease digestion at about 50° C. under saturated vapor pressure. The reaction time may be in the range of 30 min to 20 hours, for example, 1 hour to 8 hours, or 3 hours to 5 hours. It is preferable that the reaction be maintained under saturated vapor pressure in order to prevent evaporation of the reaction solution, but the present invention is not limited to this configuration.

Step (b) may be configured to include stirring the reaction solution, so as to facilitate the contact of the porous body with the nanoparticles, and the stirring may be conducted over the whole reaction time, or only during part of the reaction time such as only during a reaction initial stage, and therefore the stirring is not limited to particular duration and timing.

Peptides obtained by the protease digestion are dissolved and released in the reaction solution. Therefore, in order to subject a target peptide fragment to mass spectrometry, it is necessary to remove the porous body and the nanoparticles. This can be achieved by subjecting a sample after the protease digestion to filtration, centrifugation, magnetic separation, dialysis, and the like.

For example, by filtration using a filtration membrane made of polyvinylidene fluoride (PVDF) (low-binding hydrophilic PVDF having a pore diameter of 0.2 μm manufactured by Millipore Corporation), a filtration membrane made of polytetrafluoroethylene (PTFE) (low-binding hydrophilic PTFE having a pore diameter of 0.2 μm manufactured by Millipore Corporation), and the like, the porous body and the nanoparticles can be easily removed. The filtration may be centrifugal filtration, thereby making it possible to carry out the filtration promptly and easily.

<Step (c)>

Step (c) of the method according to the present invention is a step of detecting, by using liquid chromatography mass spectrometry (LC-MS), the peptide fragments obtained by the selective protease digestion.

An ionization method in mass spectrometry and an analysis method of ionized sample are not particularly limited. Further, MS/MS analysis, multistage mass spectrometry of MS3 or higher, or multiple reaction monitoring (MRM) can also be performed using a triple quadrupole mass spectrometer or the like.

Examples of an apparatus especially suitable for the method of the present invention include, but not limited to, LCMS-8030, LCMS-8040, LCMS-8050, LCMS-8060 (all from Shimadzu Corporation), and LCMS-IT-TOF (Shimadzu Corporation).

With the mass spectrometry or the like to detect a peptide fragment including an amino acid sequence of a Fab region specific to a target monoclonal antibody, for example, CDR1 region, CDR2 region, or CDR3 region of a heavy chain and/or a light chain, it is possible to identify or quantify the target monoclonal antibody.

Amino acid sequence information and the like of monoclonal antibodies intended to be used as an antibody medicine have been published, so that information of amino acid sequences of heavy chains and light chains, Fab and Fc domains, complementarity determining regions (CDRs), disulphide bonding, etc. are available. The protease digestion according to the nSMOL method produces a plurality of peptides, and if amino acid sequence information of each of the peptides is available, it can be easily understood at which position in the monoclonal antibody the peptide exists. Therefore, it is possible to select an especially suitable peptide as an analysis target from among a plurality of peptides derived from Fab regions. Such a peptide thus selected is called "signature peptide."

The peptide fragments to be detected by LC-MS are preferably those derived from a heavy chain in the method according to the present invention, but not particularly limited.

Details of nSMOL method are disclosed, for example, in WO2015/033479; WO2016/143223; WO2016/143224; WO2016/143226; WO2016/143227; WO2016/194114; Analyst. 2014 Feb. 7; 139(3): 576-80. doi: 10.1039/c3an02104a; Anal. Methods, 2015; 21: 9177-9183. doi: 10.1039/c5ay01588j; Drug Metabolism and Pharmacokinetics, 2016; 31: 46-50. doi:10.1016/j.dmpk.2015.11.004; Bioanalysis. 2016; 8(10):1009-20. doi: 10.4155. bio-2016-0018; Biol Pharm Bull, 2016; 39(7):1187-94. doi: 10.1248/bpb.b16-00230; J Chromatogr B Analyt Technol Biomed Life Sci; 2016; 1023-1024:9-16. doi: 10.1016/j.jchromb.2016.04.038; Clin Pharmacol Biopharm 2016; 5:164. doi:10.4172/2167-065X.1000164; and J. Pharm Biomed Anal; 2017; 145:33-39. doi:10.1016/j.jpba.2017.06.032; and the like. The contents disclosed in these literatures are incorporated herein by reference.

The nSMOL® Antibody BA kit, which is commercially available as "nSMOL Antibody BA Kit" from Shimadzu Corporation with an instruction manual, includes the following reagents.

Immunoglobulin Collection Resin (suspension of a porous body according to the present invention)
Wash Solution 1 (washing solution)
Wash Solution 2 (washing solution)
Reaction Solution (reaction solution)
Enhanced Reaction Solution (reaction accelerating solution)
Reaction Stop Solution (reaction terminating solution)
FG Beads Trypsin DART® (suspension of nanoparticles (particle diameter: 200 nm) with protease immobilized thereon)

One example of a conventional protocol of the nSMOL method is as below.

<Step (a)>
1. Dilute a biological sample of 5 to 10 μL containing a monoclonal antibody with PBS+0.1% n-octyl thioglycoside (OTG) in an amount larger than the amount of the sample by about 10 to 20 times.
2. Add 250 μL of Immunoglobulin Collection Resin (TOYOPEARL AF-rProtein A HC-650F, 50% slurry).
3. Gently conduct vortex stirring to the sample solution for about 5 min.
4. Collect the whole sample solution with ultrafree low-protein binding Durapore PFDF (0.22 μm).
5. Conduct centrifugal separation to remove supernatant (10,000 g×1 min).
6. Add 300 μL of PBS+0.1% OTG therein, and conduct centrifugal separation to remove supernatant (10,000 g×1 min).
7. Repeat step 6.
8. For removing the surfactant, add 300 μL of PBS therein, and conduct centrifugal separation to remove supernatant (10,000 g×1 min).
9. Repeat step 8.
10. Add 75 to 100 μL of Reaction Solution or Enhanced Reaction Solution, in which 10 fmol/μL of P14R synthetic peptide have been added in advance.

<Step (b)>
11. Add 5 to 10 μL of FG beads on which chemically-modified trypsin is immobilized (0.5 mg/ml FG beads suspension).
12. Conduct the reaction for 4 to 6 hours, gently stirring the reaction solution at 50° C. under saturated vapor pressure.
13. Add 10 μL of 10% formic acid therein to terminate the reaction.
14. Conduct centrifugal filtration (10,000 g×1 min) to collect a solution.
15. Place the solution on a magnetic stand and let the solution stand for about 1 to 2 min, thereby removing excess resin.

<Step (c)>
16. Conduct LCMS analysis of the solution.

The step (a') in the method according to the present invention may be conducted after the step (a) described above. More accurately, the addition of the reducing agent for conducting the step (a') may be conducted at any timing during the process between "4." and "8." above, in which timing the monoclonal antibody in the biological sample is considered to have been immobilized in the pores of the porous body (Immunoglobulin Collection Resin) in the step (a). In this way, the monoclonal antibody immobilized in the pores of the porous body can be subjected to the reaction with the reducing agent, and the reducing agent can be removed before the protease digestion conducted in the step (b). If necessary, the method may further include an additional step(s) such as a washing step.

Tocilizumab, which is described herein as one example of the monoclonal antibodies with a rigid structure, is a humanized monoclonal antibody that can bind specifically with Interleukin-6, and is commercially available under the product name "Actemra."

Mogamulizumab, which is also considered as having a rigid structure, is a humanized monoclonal antibody that can bind specifically with CC Chemokine Receptor Type 4, and is commercially available under the product name "Poteligeo."

Mepolizumab, which is also considered as having a rigid structure, is a humanized monoclonal antibody that can bind specifically with Interleukin-5, and is commercially available under the product name "Nucala."

As described above, the method according to the present invention is especially advantageous for the nSMOL method-based detection of a monoclonal antibody with a rigid structure, but may be employed for any types of monoclonal antibodies. However, the method of the present invention comprises additional steps in the conventional method, thereby prolonging the measurement time and using extra reagents. Therefore, it is recommended to select the method according to the present invention, especially in the case where the detection results by the conventional nSMOL method are significantly lower than expected, or in the case where the Fab region of a monoclonal antibody to be measured is expected to have a rigid structure.

For example, the method according to the present invention is applicable to, but not limited to, not only monoclonal antibodies that are difficult to be detected at a concentration of 0.5 μg/mL or lower, 1 μg/mL or lower, 5 μg/mL or lower, or 10 μg/mL or lower with the conventional nSMOL method, and are not detectable within a concentration range sufficiently lower than the quantifiable range expected from results of pharmacokinetic studies, but also monoclonal antibodies that are detectable within such a concentration range.

Concrete examples of the monoclonal antibodies to which the method according to the present invention is suitably applied include, but not limited to, Tocilizumab, Mogamulizumab, and Mepolizumab, which are also described in Examples below.

EXAMPLES

The present invention will be described more concretely, referring to the following Examples, but the present invention is not limited to the Examples.

Example 1

Using Tocilizumab as the target of measurement, a protocol for a method of detecting Tocilizumab in a sample was studied, using the "nSMOL. Antibody BA Kit" (Shimadzu Corporation).

Into 12.5 µL of Immunoglobulin Collection Resin suspension included in the kit, 90 µL of Wash Solution 1 included was added. Into this suspension, 5 µL of a sample was added, where the sample had been prepared by adding Tocilizumab (Chugai Pharmaceutical Co., Ltd.) in human plasma (manufactured by KOHJIN BIO Corporation, filtered with a 5-µm filter and then with a 0.8-µm filter) to make up 100 µg/mL, and the suspension was stirred gently for about 5 min (step (a)).

The suspension thus prepared was transferred into a filter cup, and centrifuged (10,000 g×1 min) to remove the supernatant.

5 mM, 50 mM, 100 mM, 250 mM, or 500 mM of TCEP-HCL (Sigma-Aldrich Co. LLC) aqueous solution was added or not added therein, and the samples were then let stand for 30 min at room temperature (at pH 1.5 to 2.5, the step (a')).

After removing supernatant by centrifugation (10,000 g×1 min), 300 µL of Wash Solution 1 was added therein. This operation was repeated three times.

300 µL of Wash Solution 2 was added therein, and the samples were centrifuged. This operation was repeated 3 times.

Into the samples, 80 of Reaction Solution was added, 5 µL of FG beads Trypsin DART was further added, and reaction was conducted at 50° C. under saturated vapor pressure for 5 hours (step (b)).

After 5 µL of Reaction Stop Solution was added therein, the samples were centrifuged, and subjected to magnetic separation, thereby collecting a solution.

Using NexeraX2 system (Shimadzu Corporation) and LCMS-8050/8060 (Shimadzu Corporation), LCMS analysis was conducted (step (c)).

The measurement was conducted for each of 5 peptides listed in Table 1 below, which were selected as monitor peptides existing in the Fab region on the basis of amino acid sequences of heavy chain and light chain of Tocilizumab.

Figure 1:
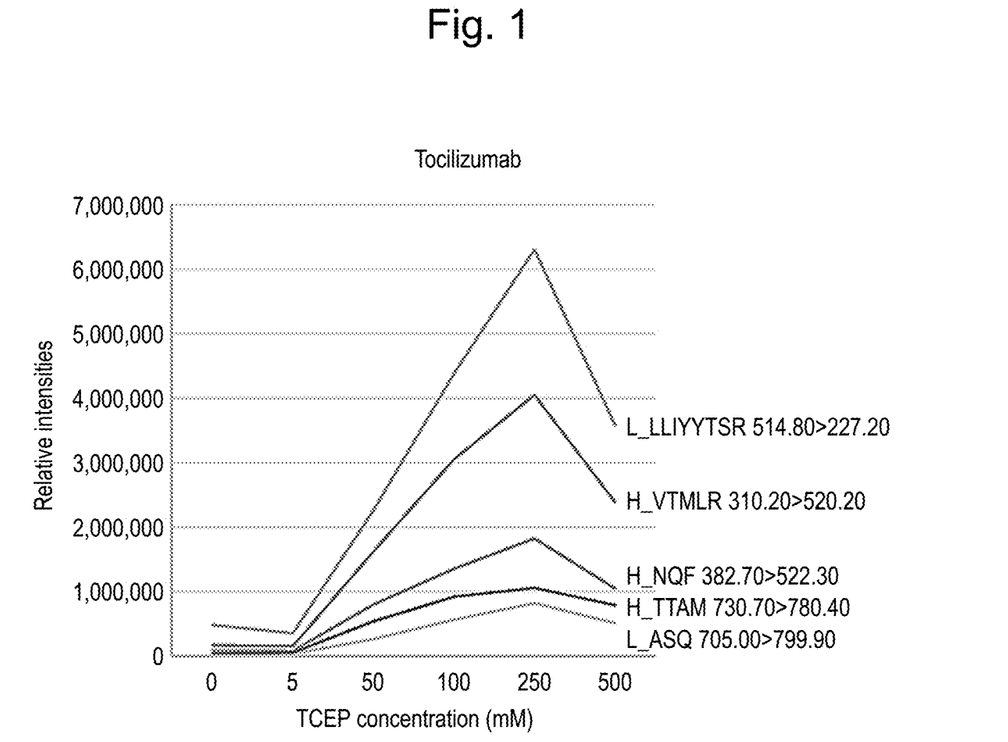
FIG. 1 illustrates how the detection results by the nSMOL method for a plurality of peptides derived from Tocilizumab are improved by addition of TCEP.

As demonstrated in the results illustrated in FIG. 1, the detection results of the samples with TCEP for each of the peptides were improved compared with the sample without TCEP in dependence upon the concentrations of TCEP, and the highest relative peak intensity was obtained in the sample with 250 mM TCEP.

Example 2

In order to confirm whether or not the antibody molecule (Tocilizumab) was dissociated from the porous body by the TCEP addition, 250 mM of TCEP (pH 1.5 or pH 7.0) was added into a suspension of the Immunoglobulin Collection Resin on which the antibody molecules were retained, and the suspension was let stand at room temperature for 30 min. After that, a solution (flow through) and a protein on the protein A beads were separated by SDS-PAGE. As a control, a sample with 25 mM Tris-HCl (pH 8.0) added therein was let stand in a similar manner and subjected to electrophoresis. Results are shown in FIG. 2.

Figure 2:
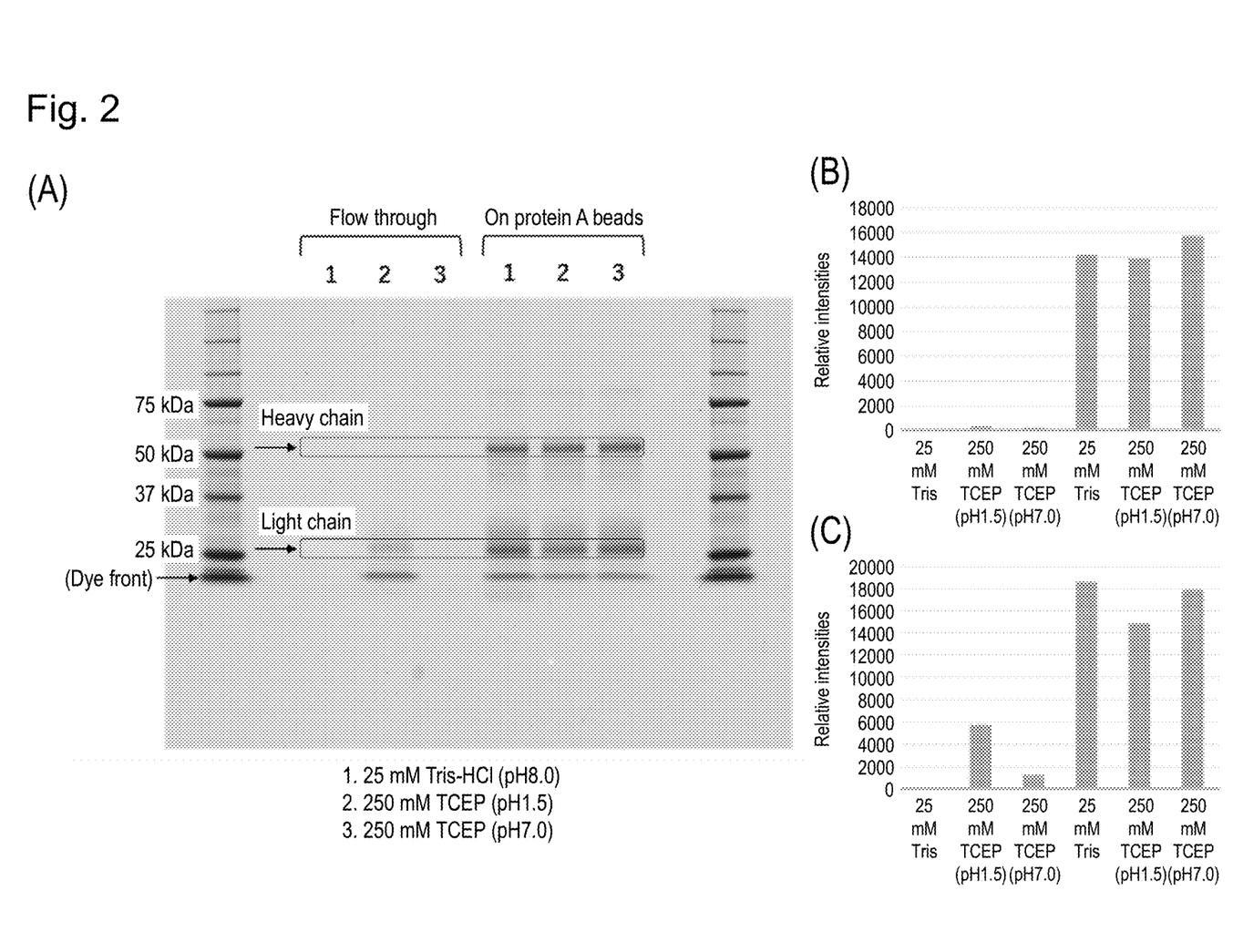
FIG. 2 illustrates that the antibody is not dissociated from a porous body by reaction in the presence of TCEP.

As understood from the bands of the heavy chain and the light chain in FIG. 2(A), very little dissociation from the porous body was observed in the heavy chain under any of the conditions (FIG. 2(B)). For the light chains, some dissociation was observed at pH 1.5 with 250 mM TCEP, but the dissociation was very limited at pH 7.0 (FIG. 2(C)). These results suggest the possibility that, under strong acidic conditions, the light chain binding to the heavy chain via SS bond would be dissociated by about 30%.

Example 3

VTMLR (SEQ ID NO: 2), which is a peptide derived from the heavy chain showing a good detection result in Example 1 was selected as a signature peptide, and measurement was conducted with a sample in which 250 mM TCEP was added under similar conditions as in Example 1 (pH 1.5 or pH 7.0).

Figure 3:
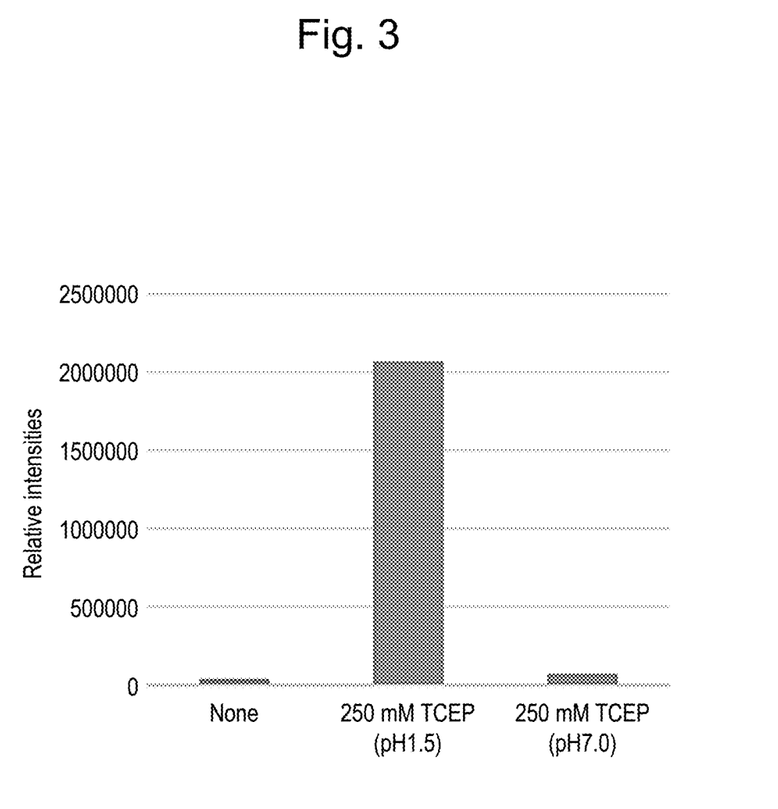
FIG. 3 illustrates detection results of VTMLR (SEQ ID NO: 1) in the presence of 250 nM TCEP (at pH 1.5 and pH 7) or in the absence of TCEP.

As a result, as illustrated in FIG. 3, the detection results of the samples with TCEP were not significantly different from the sample without TCEP under neutral condition of pH 7.0, but it was demonstrated that the detection results were significantly improved under strong acidic condition of pH 1.5.

Example 4

Detection results were compared with samples in which 250 mM TECP was added (pH 1.5) but the time length for letting stand at room temperature (reduction reaction time) were varied. The measurement was conducted similarly as in Example 1 with VTMLR (SEQ ID NO: 2) as a signature peptide.

TABLE 1

| Sequence position | Amino acid sequence | SEQ ID NO. | MRM transition |
|---|---|---|---|
| Heavy chain, 68-72 | VTMLR | 1 | 310.20 > 520.20 |
| Heavy chain, 77-82 | NQFSLR | 2 | 382.70 > 522.30 |
| Light chain, 46-53 | LLIYYTSR | 3 | 514.80 > 227.20 |
| Light chain, 35-42 | ASQDISSYLNWYQQKPGK | 4 | 705.00 > 799.90 |
| Heavy chain, 103-123 | TTAMDYVVGQGSLVTVSSASTK | 5 | 730.70 > 780.40 |

Figure 4:
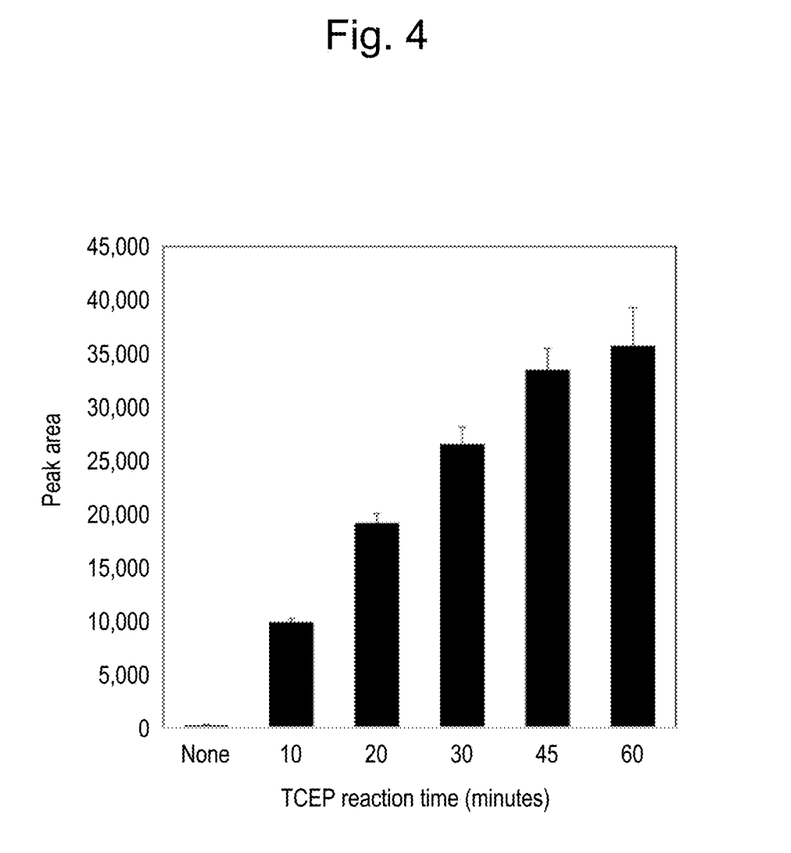
FIG. 4 illustrates that a detected amount of a peptide derived from Tocilizumab increases in dependence upon a time length of a reduction reaction caused by TCEP addition.

As a result, as illustrated in FIG. 4, it was observed that the detection result with 10-min reduction reaction was significantly increased compared with the sample without TCEP, and higher detection values were obtained depending on the length of the reaction time, by further prolonging the reaction time up to 60 min.

Example 5

Whether or not the detection results can be improved with 250 mM TCEP (pH 1.5) at low antibody concentrations was confirmed with various amounts of Tocilizumab added in the plasma. The measurement was conducted similarly as in Example 1 with VTMLR (SEQ ID NO: 2) as a signature peptide.

As illustrated in Table 2, the low concentrations up to 1 μg/mL in the samples could not be detected by the nSMOL method in the case where steps of adding a reaction acceleration solution (Enhanced Reaction Solution in the kit) instead of 250 mM TCEP (pH 1.5) and letting the sample stand for 30 min were added. On the other hand, it was demonstrated that Tocilizumab at the concentration of 0.25 μg/mL or higher in the sample could be detected and quantified in the case where the steps of adding 250 mM TCEP (pH 1.5) and letting the sample stand for 30 min were added (the step (a') of the present invention).

TABLE 2

H_VTMLR 310.20 > 520.20
Peak area

| Tocilizumab (μg/mL) | Reaction accelerating solution | 250 mM TCEP |
|---|---|---|
| 0 | ND | 375 |
| 0.25 | ND | 3362 |
| 0.5 | ND | 6853 |
| 1 | ND | 12942 |
| 5 | 792 | 57092 |
| 25 | 4532 | 251402 |
| 50 | 9351 | 497512 |
| 100 | 19003 | 1014810 |

Example 6

Samples containing Tocilizumab in a concentration range of 0.25 to 300 μg/mL were analyzed under similar conditions as in Example 1, except that the step of adding 250 mM TCEP (pH 1.5) and letting the sample stand for 30 min was included. The measurement was conducted similarly as in Example 1 with VTMLR (SEQ ID NO: 2) as a signature peptide.

Figure 5:
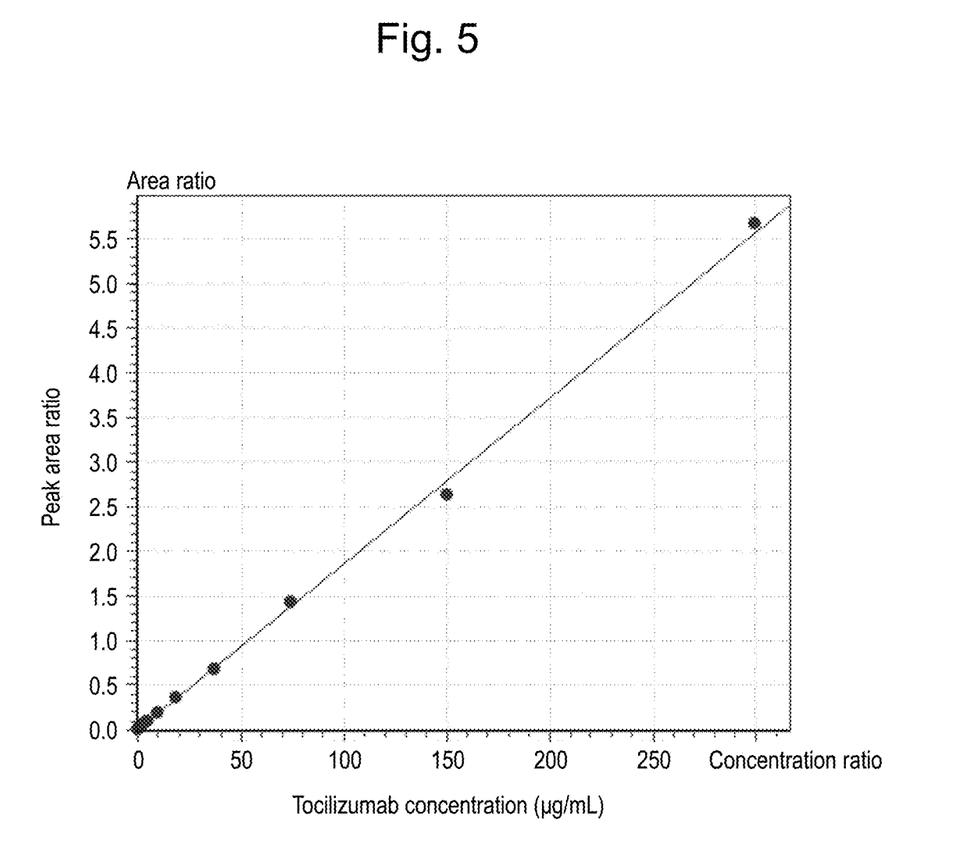
FIG. 5 illustrates a calibration curve prepared in the detection of Tocilizumab by the method according to the present invention.

As a result, as illustrated in FIG. 5, a substantially linear quantification results in proportion with the concentration was obtained (r=0.99), and the analysis guideline standard was achieved. This demonstrated that the method according to the present invention is a highly reliable analysis method.

Example 7

Measurement was conducted under similar conditions as in Example 1, except that the steps of adding 250 mM TCEP (pH 1.5) and letting the sample stand for 30 min were included, using various antibodies. For each of Cetuximab (Bristol-Myers Squibb Company), Rituximab (Zenyaku Kogyo Company, Limited), Brentuximab (Takeda Pharmaceutical Company Limited), Ipilimumab (Ono Pharmaceutical Co., Ltd.), Nivolumab (Ono Pharmaceutical Co., Ltd.), Bevacizumab (Chugai Pharmaceutical Co., Ltd.), Adalimumab (AbbVie Inc.), Trastuzumab (Chugai Pharmaceutical Co., Ltd.), Ramucirumab (Eli Lilly Japan K.K.), Infliximab (Mitsubishi Tanabe Pharma Corporation), Mepolizumab (GlaxoSmithKline K.K.), and Mogamulizumab (Kyowa Kirin Co., Ltd.), signature peptides listed in Table 3 were selected on the basis of the amino acid sequence information and the like, and detection results were compared between samples with and without 250 mM TCEP (pH 1.5).

The results in Table 3 are relative results for these antibodies with respect to the samples without the addition of 250 mM TCEP (pH 1.5) (control), where the detection results for the control are 1.

As understood from Table 3, the detection results of Tocilizumab, Mepolizumab and Mogamulizumab were increased by several ten times by the reduction reaction under acidic condition with the addition of 250 mM TCEP (pH L5). This suggests that these molecules having a relatively rigid structure and thereby having tolerance against the protease digestion in the nSMOL method become susceptible to the digestion by the presence of TCEP under strong acidic condition, providing such a large improvement of the detection result. On the other hand, other antibodies did not show a significant effect, even though the detection results were improved to some extent. However, these other antibodies have already been confirmed to provide sufficiently reliable detection in the conventional nSMOL method and satisfy the guideline standards for the validation of the biological analysis method. Regarding lower detection results for Adalimumab and Ramucirumab than controls, the signature peptides for these antibodies are derived from the light chain, and it is deduced that the light chain may possibly be dissociated from the porous body before the protease digestion because of the presence of the TCEP under strong acidic condition.

TABLE 3

| Antibody | Signature peptide | SEQ ID NO. | Control | 250 mM TCEP |
|---|---|---|---|---|
| Cetuximab | SQVFFK | 6 | 1 | 0.75 |
| Rituximab | GLEWIGAIYPGNGDTSYNQK | 7 | 1 | 1.75 |
| Brentuximab | VLIYAASNLESGIPAR | 8 | 1 | 3.63 |
| Ipilimumab | ASQSVGSSTAWYQQKPGQAPR | 9 | 1 | 0.61 |
| Nivolumab | ASGITFSNSGMHWVR | 10 | 1 | 1.53 |
| Bevacizumab | FTFSLDTSK | 11 | 1 | 0.83 |

TABLE 3-continued

| Antibody | Signature peptide | SEQ ID NO. | Control | 250 mM TCEP |
|---|---|---|---|---|
| Adalimumab | APYTFGQGTK | 12 | 1 | 0.23 |
| Trastuzumab | IYPTNGYTR | 13 | 1 | 2.81 |
| Ramucirumab | AFPPTFGGGTK | 14 | 1 | 0.21 |
| Infliximab | SINSATHYAESVK | 15 | 1 | 1.46 |
| Mepolizumab | GLEWLGVIWASGGTDYNSALMSR | 16 | 1 | 19.53 |
| Mogamulizumab | VEDTALYYCGR | 17 | 1 | 32.16 |
| Tocilizumab | VTMLR | 1 | 1 | 54.42 |

INDUSTRIAL APPLICABILITY

The present invention improves the protocol of the nSMOL method, and further applicability of the versatility of the detection method for the monoclonal antibodies using mass spectrometry is expected. Especially, the present invention gives the nSMOL method a wider applicability in pharmacokinetic studies and therapeutic drug monitoring studies.

All publications, patents and patent applications cited in the present specification are incorporated herein by reference in their entirety.

The invention claimed is:

1. A detection method for a monoclonal antibody in a sample, comprising:
   (a) capturing monoclonal antibodies in a sample to immobilize the monoclonal antibodies in pores of a porous body, wherein the porous body has Protein A, which functions as a linker molecule to site-specifically interactive with the monoclonal antibody, immobilized in the pores;
   (b) bringing the porous body in which the monoclonal antibodies are immobilized into contact with nanoparticles on which protease is immobilized to conduct selective protease digestion of the monoclonal antibodies, wherein the protease is trypsin; and
   (c) detecting, by a liquid chromatography mass spectrometry (LC-MS), peptide fragments obtained by the selective protease digestion;
   wherein the method further comprises, after the step (a):
   (a') adding a reducing agent and conducting a reduction reaction under a strong acidic condition of a pH of 2.5 or lower; and
   (a") removing the reducing agent after conducting the reduction reaction and before conducting the selective protease digestion,
   wherein the reducing agent is Tris(2-carboxyethyl) phosphine (TCEP), or a hydrochloride salt thereof in a range of 100 to 500 mM.

2. The method according to claim 1, wherein a time length of the reduction reaction of the step (a') is in a range of 10 to 60 min.

3. The method according to claim 1, wherein the peptide fragments to be detected by the LC-MS are derived from a heavy chain.

4. The method according to claim 1, wherein the monoclonal antibody is selected from the group consisting of rituximab, brentuximab, nivolumab, trastuzumab, infliximab, mepolizumab, mogamulizumab and tocilizumab.

* * * * *

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial
<220> FEATURE:
<223> OTHER INFORMATION: Tocilizumab monitor peptide

<400> SEQUENCE: 1

Val Thr Met Leu Arg
1               5

<210> SEQ ID NO 2
<211> LENGTH: 6
<212> TYPE: PRT
<213> ORGANISM: Artificial
<220> FEATURE:
<223> OTHER INFORMATION: Tocilizumab monitor peptide

<400> SEQUENCE: 2

Asn Gln Phe Ser Leu Arg
1               5

<210> SEQ ID NO 3
<211> LENGTH: 8
<212> TYPE: PRT
<213> ORGANISM: Artificial
<220> FEATURE:
<223> OTHER INFORMATION: Tocilizumab monitor peptide

<400> SEQUENCE: 3

Leu Leu Ile Tyr Tyr Thr Ser Arg
1               5

<210> SEQ ID NO 4
<211> LENGTH: 18
<212> TYPE: PRT
<213> ORGANISM: Artificial
<220> FEATURE:
<223> OTHER INFORMATION: Tocilizumab monitor peptide
```

-continued

```
<400> SEQUENCE: 4

Ala Ser Gln Asp Ile Ser Ser Tyr Leu Asn Trp Tyr Gln Gln Lys Pro
1               5                   10                  15

Gly Lys

<210> SEQ ID NO 5
<211> LENGTH: 21
<212> TYPE: PRT
<213> ORGANISM: Artificial
<220> FEATURE:
<223> OTHER INFORMATION: Tocilizumab monitor peptide

<400> SEQUENCE: 5

Thr Thr Ala Met Asp Tyr Trp Gly Gln Gly Ser Leu Val Thr Val Ser
1               5                   10                  15

Ser Ala Ser Thr Lys
            20

<210> SEQ ID NO 6
<211> LENGTH: 6
<212> TYPE: PRT
<213> ORGANISM: Artificial
<220> FEATURE:
<223> OTHER INFORMATION: Cetuximab signature peptide

<400> SEQUENCE: 6

Ser Gln Val Phe Phe Lys
1               5

<210> SEQ ID NO 7
<211> LENGTH: 20
<212> TYPE: PRT
<213> ORGANISM: Artificial
<220> FEATURE:
<223> OTHER INFORMATION: Rituximab signature peptide

<400> SEQUENCE: 7

Gly Leu Glu Trp Ile Gly Ala Ile Tyr Pro Gly Asn Gly Asp Thr Ser
1               5                   10                  15

Tyr Asn Gln Lys
            20

<210> SEQ ID NO 8
<211> LENGTH: 16
<212> TYPE: PRT
<213> ORGANISM: Artificial
<220> FEATURE:
<223> OTHER INFORMATION: Brentuximab signature peptide

<400> SEQUENCE: 8

Val Leu Ile Tyr Ala Ala Ser Asn Leu Glu Ser Gly Ile Pro Ala Arg
1               5                   10                  15

<210> SEQ ID NO 9
<211> LENGTH: 21
<212> TYPE: PRT
<213> ORGANISM: Artificial
<220> FEATURE:
<223> OTHER INFORMATION: Ipilimumab signature peptide

<400> SEQUENCE: 9

Ala Ser Gln Ser Val Gly Ser Ser Thr Ala Trp Tyr Gln Gln Lys Pro
1               5                   10                  15

Gly Gln Ala Pro Arg
```

```
<210> SEQ ID NO 10
<211> LENGTH: 15
<212> TYPE: PRT
<213> ORGANISM: Artificial
<220> FEATURE:
<223> OTHER INFORMATION: Nivolumab signature peptide

<400> SEQUENCE: 10

Ala Ser Gly Ile Thr Phe Ser Asn Ser Gly Met His Trp Val Arg
1               5                   10                  15

<210> SEQ ID NO 11
<211> LENGTH: 9
<212> TYPE: PRT
<213> ORGANISM: Artificial
<220> FEATURE:
<223> OTHER INFORMATION: Bevacizumab signature peptide

<400> SEQUENCE: 11

Phe Thr Phe Ser Leu Asp Thr Ser Lys
1               5

<210> SEQ ID NO 12
<211> LENGTH: 10
<212> TYPE: PRT
<213> ORGANISM: Artificial
<220> FEATURE:
<223> OTHER INFORMATION: Adalimumab signature peptide

<400> SEQUENCE: 12

Ala Pro Tyr Thr Phe Gly Gln Gly Thr Lys
1               5                   10

<210> SEQ ID NO 13
<211> LENGTH: 9
<212> TYPE: PRT
<213> ORGANISM: Artificial
<220> FEATURE:
<223> OTHER INFORMATION: Trastuzumab signature peptide

<400> SEQUENCE: 13

Ile Tyr Pro Thr Asn Gly Tyr Thr Arg
1               5

<210> SEQ ID NO 14
<211> LENGTH: 11
<212> TYPE: PRT
<213> ORGANISM: Artificial
<220> FEATURE:
<223> OTHER INFORMATION: Ramcirumab signature peptide

<400> SEQUENCE: 14

Ala Phe Pro Pro Thr Phe Gly Gly Gly Thr Lys
1               5                   10

<210> SEQ ID NO 15
<211> LENGTH: 13
<212> TYPE: PRT
<213> ORGANISM: Artificial
<220> FEATURE:
<223> OTHER INFORMATION: Infliximab signature peptide

<400> SEQUENCE: 15

Ser Ile Asn Ser Ala Thr His Tyr Ala Glu Ser Val Lys
1               5                   10
```

```
<210> SEQ ID NO 16
<211> LENGTH: 23
<212> TYPE: PRT
<213> ORGANISM: Artificial
<220> FEATURE:
<223> OTHER INFORMATION: Mepolizumab signature peptide

<400> SEQUENCE: 16

Gly Leu Glu Trp Leu Gly Val Ile Trp Ala Ser Gly Gly Thr Asp Tyr
1               5                   10                  15

Asn Ser Ala Leu Met Ser Arg
            20

<210> SEQ ID NO 17
<211> LENGTH: 11
<212> TYPE: PRT
<213> ORGANISM: Artificial
<220> FEATURE:
<223> OTHER INFORMATION: Mogamulizumab signature peptide

<400> SEQUENCE: 17

Val Glu Asp Thr Ala Leu Tyr Tyr Cys Gly Arg
1               5                   10
```